US010195390B2

(12) United States Patent
Koeppel

(10) Patent No.: US 10,195,390 B2
(45) Date of Patent: Feb. 5, 2019

(54) OXYGEN CONCENTRATOR WITH DYNAMIC NOISE CONTROL

(75) Inventor: Bradley Stewart Koeppel, Smyrna, GA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 161 days.

(21) Appl. No.: 14/343,403

(22) PCT Filed: Sep. 4, 2012

(86) PCT No.: PCT/IB2012/054556
§ 371 (c)(1),
(2), (4) Date: Mar. 7, 2014

(87) PCT Pub. No.: WO2013/038297
PCT Pub. Date: Mar. 21, 2013

(65) Prior Publication Data
US 2014/0216461 A1 Aug. 7, 2014

Related U.S. Application Data

(60) Provisional application No. 61/533,864, filed on Sep. 13, 2011.

(51) Int. Cl.
*A61M 16/20* (2006.01)
*A61M 16/00* (2006.01)
(Continued)

(52) U.S. Cl.
CPC ........ *A61M 16/20* (2013.01); *A61M 16/0057* (2013.01); *A61M 16/0063* (2014.02);
(Continued)

(58) Field of Classification Search
CPC ............ A61M 16/101; A61M 16/0677; A61M 2016/0021; A61M 2016/0039; A61M 2016/1025; A61M 16/00; A61M 16/0057; A61M 16/0063; A61M 16/10; A61M 16/105; A61M 16/20; A61M 16/201; B01D 2256/12; B01D 2259/402; B01D 2259/4533
(Continued)

(56) References Cited

U.S. PATENT DOCUMENTS 3,182,435 A 5/1965 Axt
4,349,357 A 9/1982 Russell
(Continued)

FOREIGN PATENT DOCUMENTS

CN 201049886 Y 4/2008
CN 201772114 U 3/2011
(Continued)

*Primary Examiner* — Colin W Stuart
(74) *Attorney, Agent, or Firm* — Michael W. Haas

(57) ABSTRACT

An oxygen concentrator an inlet opening configured to receive air. The concentrator also includes a compressor configured to pressurize the air received through the inlet opening. An inlet opening restrictor is configured to dynamically change a characteristic of the inlet opening responsive to increased or decreased demand for the pressurized air. The concentrator further includes a sieve bed configured to separate the pressurized air into a concentrated gas component for delivery to a subject.

18 Claims, 9 Drawing Sheets

US 10,195,390 B2
Page 2

(51) Int. Cl.
*C01B 13/02* (2006.01)
*B01D 53/04* (2006.01)
*A61M 16/06* (2006.01)
*A61M 16/10* (2006.01)

(52) U.S. Cl.
CPC ...... *A61M 16/0677* (2014.02); *A61M 16/101* (2014.02); *B01D 53/0446* (2013.01); *C01B 13/0259* (2013.01); *A61M 16/107* (2014.02); *A61M 2016/0021* (2013.01); *A61M 2016/0039* (2013.01); *A61M 2016/1025* (2013.01); *A61M 2205/42* (2013.01); *B01D 2256/12* (2013.01); *B01D 2259/402* (2013.01); *B01D 2259/4533* (2013.01)

(58) Field of Classification Search
USPC ....... 251/129.08, 149.8, 153, 208, 209, 226, 251/227, 231, 236, 309, 313, 352, 354
See application file for complete search history.

(56) References Cited

U.S. PATENT DOCUMENTS

| | | | |
|---|---|---|---|
| 5,099,837 A | 3/1992 | Russel, Sr. | |
| 5,906,203 A * | 5/1999 | Klockseth | A62B 18/006 128/201.25 |
| 6,006,748 A * | 12/1999 | Hollis | A61M 16/208 128/204.18 |
| 7,794,533 B2 | 9/2010 | Bliss | |
| 2003/0127096 A1* | 7/2003 | McAuliffe | A61M 16/00 128/204.18 |
| 2004/0131489 A1 | 7/2004 | Leu | |
| 2005/0103342 A1 | 5/2005 | Jorczak | |
| 2005/0279212 A1* | 12/2005 | Amann | B01D 46/0023 96/380 |
| 2006/0117957 A1 | 6/2006 | McCombs | |
| 2007/0221225 A1 | 9/2007 | Kutt | |
| 2008/0053310 A1* | 3/2008 | Bliss | A61M 16/10 96/115 |
| 2009/0065007 A1 | 3/2009 | Wilkinson | |
| 2010/0237265 A1 | 9/2010 | Jorczak | |
| 2011/0308515 A1* | 12/2011 | Snyder | A61M 15/0065 128/200.21 |

FOREIGN PATENT DOCUMENTS

| | | |
|---|---|---|
| EP | 0124981 A2 | 11/1984 |
| EP | 1911972 A1 | 4/2008 |
| GB | 2154464 A | 9/1985 |
| JP | H04246366 A | 9/1992 |
| JP | H0245203 A | 9/1998 |
| JP | 2010017476 A | 1/2010 |
| WO | WO2013038299 A1 | 3/2013 |
| WO | WO2013038315 A1 | 3/2013 |
| WO | WO2013038319 A1 | 3/2013 |

* cited by examiner

OXYGEN CONCENTRATOR WITH DYNAMIC NOISE CONTROL

CROSS-REFERENCE TO RELATED APPLICATIONS

This patent application claims the priority benefit under 35 U.S.C. § 317 of international patent application No. PCT/IB2012/054556 filed Sep. 4, 2012, which claims the priority benefit under 35 U.S.C. § 119(e) of U.S. Provisional Application No. 61/533,864 filed on Sep. 13, 2011, the contents of which are herein incorporated by reference.

BACKGROUND OF THE INVENTION

1. Field of the Invention

The present disclosure pertains to noise reduction in oxygen concentrators.

2. Description of the Related Art

Oxygen concentrators are used to provide supplemental oxygen to improve the comfort and/or quality of life of subjects. Oxygen concentrators may be stationary and may include oxygen lines in hospitals or other facilities that provide oxygen to patients. Oxygen concentrators may also be portable to provide ambulatory patients with oxygen while away from the stationary systems.

Oxygen concentrators, especially portable oxygen concentrators, typically emit a high level of noise. The noise level increases as oxygen demand increases. Sound damping materials, such as foam, is known to be provided in the inside of the unit to lower the sound level output by absorbing as much sound and vibration as possible. However, the foam in the portable devices can increase the overall size and weight of the device, thus making the device less convenient to carry around.

SUMMARY OF THE INVENTION

Accordingly, it is an aspect of one or more embodiments of the present disclosure to provide an oxygen concentrator including an air supply and an inlet opening configured to receive air from the air supply. The concentrator further includes a compressor configured to pressurize the air received through the inlet opening and an inlet opening restrictor configured to dynamically change a characteristic of the inlet opening responsive to increased or decreased demand for the pressurized air by a subject. The concentrator also includes a sieve bed configured to separate the pressurized air into a concentrated gas component for delivery to the subject.

It is yet another aspect of one or more embodiments of the present disclosure to provide a method of reducing noise level in an oxygen concentrator, the method including the steps of receiving air from an air supply, the air being received by an inlet opening and pressurizing the air received from the air supply, the air being pressurized by a compressor. The method also includes changing a characteristic of the inlet opening responsive to increased or decreased demand for the pressurized air by a subject, the characteristic being changed by an inlet opening restrictor. The method further includes separating the pressurized air into a concentrated gas component for delivery to the subject, the separation being provided by a sieve bed.

It is yet another aspect of one or more embodiments of the present disclosure to provide a system configured to concentrate oxygen that includes means for receiving air from an air supply, the air being received by an inlet opening and means for pressurizing the air received from the air supply, the air being pressurized by a compressor. The system also includes means for changing a characteristic of the inlet opening responsive to increased or decreased demand for the pressurized air by a subject, the changing of the characteristic of the inlet opening being provided by an inlet opening restrictor; and means for separating the pressurized air into a concentrated gas component for delivery to the subject, the separation being provided by a sieve bed.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1A:
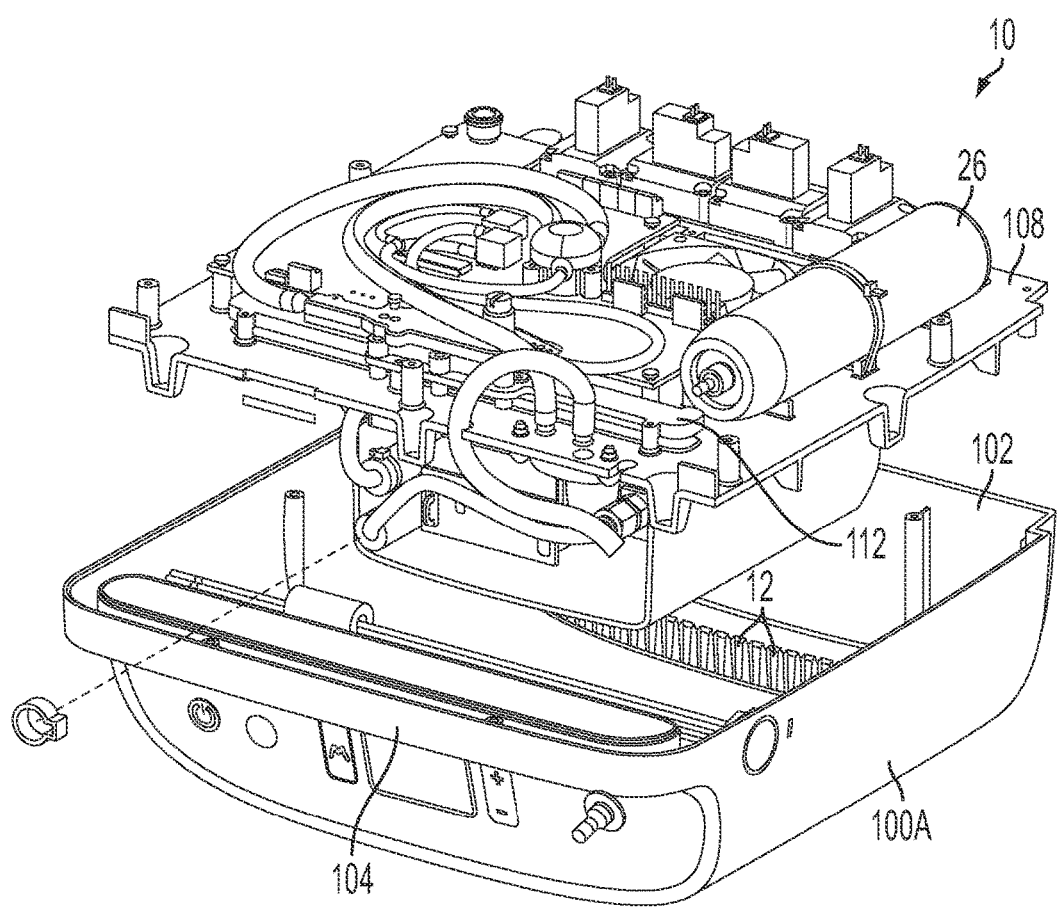
FIG. 1a is a perspective view of a housing member of a portable oxygen concentrator and one side of the support member supporting components of the portable oxygen concentrator.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1B:
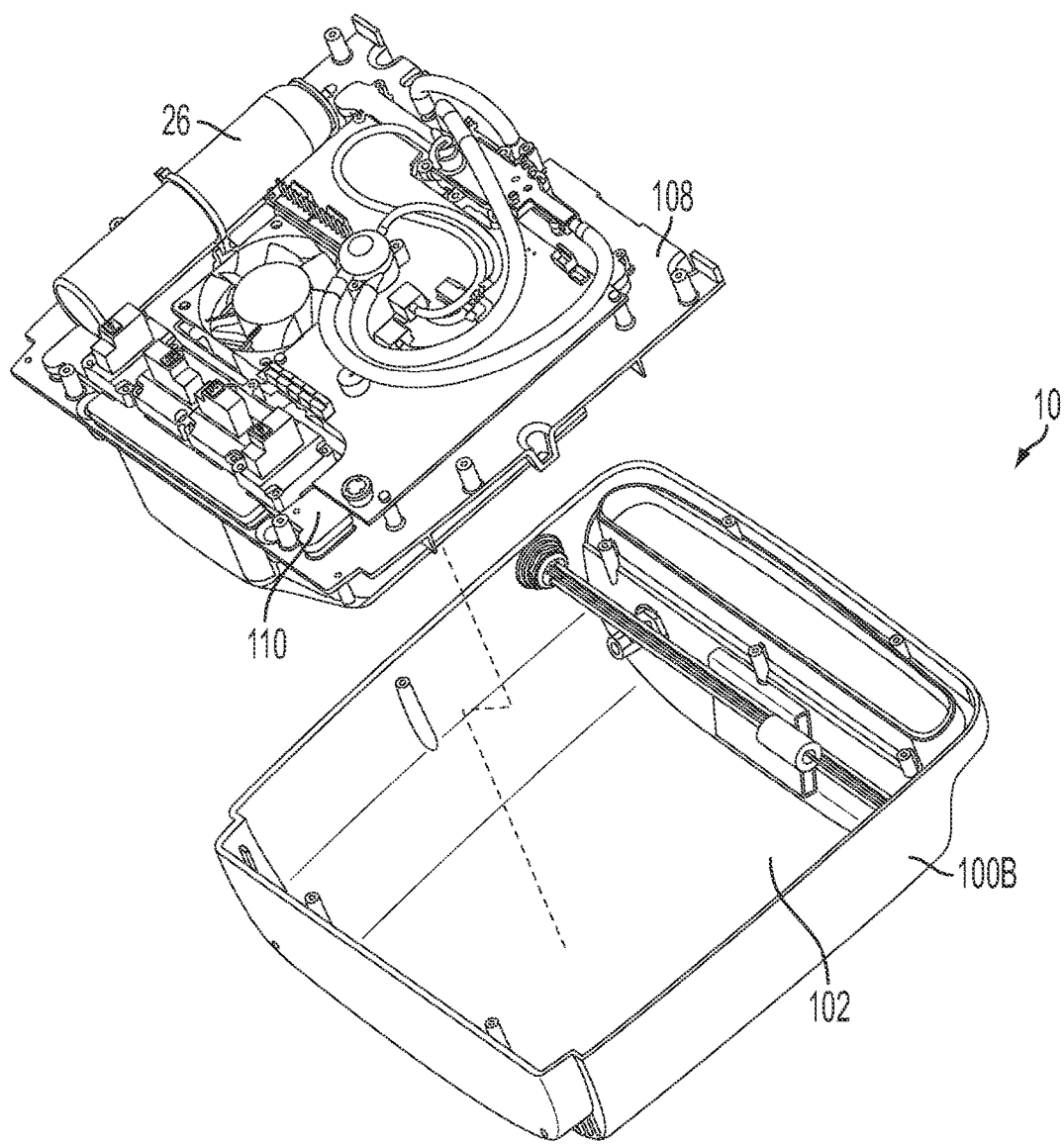
FIG. 1b is another perspective view of a housing member and the support member of the portable oxygen concentrator in accordance with an embodiment of the present disclosure.

FIGS. 1a and 1b illustrate an embodiment of a portable oxygen concentrator 10 having a housing 100 formed from two mating house members 100A, 100B cooperating with each other to define a hollow interior 102 therein. Hollow interior 102 of housing 100 may house a support member 108, which supports components of portable oxygen concentrator 10. Portable oxygen concentrator 10 may include a carrying handle 104 connected to at least one of the walls to enable portable oxygen concentrator 10 to be transported.

Housing 100 may include one or more inlet openings 12 that may communicate with interior 102 of portable oxygen concentrator 10 Inlet openings 12 are configured to allow air to pass easily through inlet openings 12, yet preventing large objects from passing therethrough.

As shown in FIGS. 1a and 1b, portable oxygen concentrator 10 includes a support member (central chassis or spine) 108. An air manifold 110 and an oxygen delivery manifold 112 of portable oxygen concentrator 10 are integrally formed or integrally molded on support member 108. Manifolds 110, 112 may contain pathways or passages for air or oxygen to travel through the concentrator, which will be described in more detail later. Additional information on an exemplary central chassis or spine with integrally formed air manifold and oxygen delivery manifold may be found in U.S. provisional patent application No. 61/533,962, filed Sep. 13, 2011, the entire disclosure of which is expressly incorporated by reference herein.

The present invention contemplates that manifolds 110, 112 are substantially rigid, e.g., thereby providing or enhancing a structural integrity of the apparatus 10. The air manifold may be formed from any engineering grade material, e.g., plastic, such as ABS, polycarbonate, and the like; metal, such as aluminum, and the like; or composite materials. The air manifold may be formed by injection molding, casting, machining, and the like.

Figure 2:
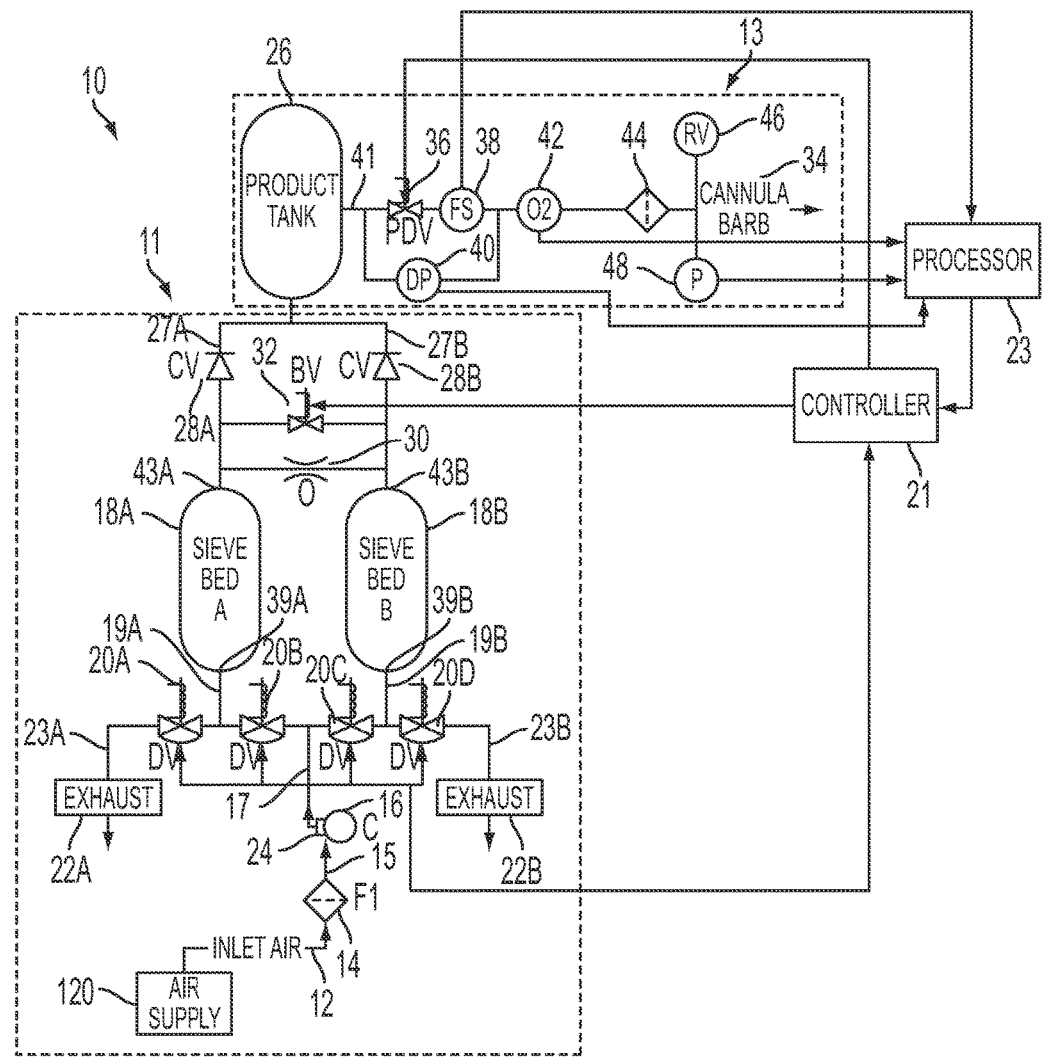
FIG. 2 schematically illustrates the portable oxygen concentrator in accordance with an embodiment of the present disclosure.

FIG. 2 is a schematic representation of an embodiment of the portable oxygen concentrator 10 having an oxygen generating system 11 and an oxygen delivery system 13. Air may enter the concentrator 10 through an opening 12 of the concentrator 10 from an air supply 120, such as ambient air. Opening 12 may be a single opening or may be a plurality of openings. Oxygen generating system 11 includes an inlet filter 14 that is provided inline between the inlet port 12 and a compressor 16 to remove dust or other particles from the ambient air drawn into the inlet port 12 before it enters the compressor 16. The filtered air may be communicated from filter 14 to an opening 24 of the compressor 16 via a compressor passage 15. Compressor 16 is configured to compress or pressurize the air to a desired pressure level.

Figure 3A:
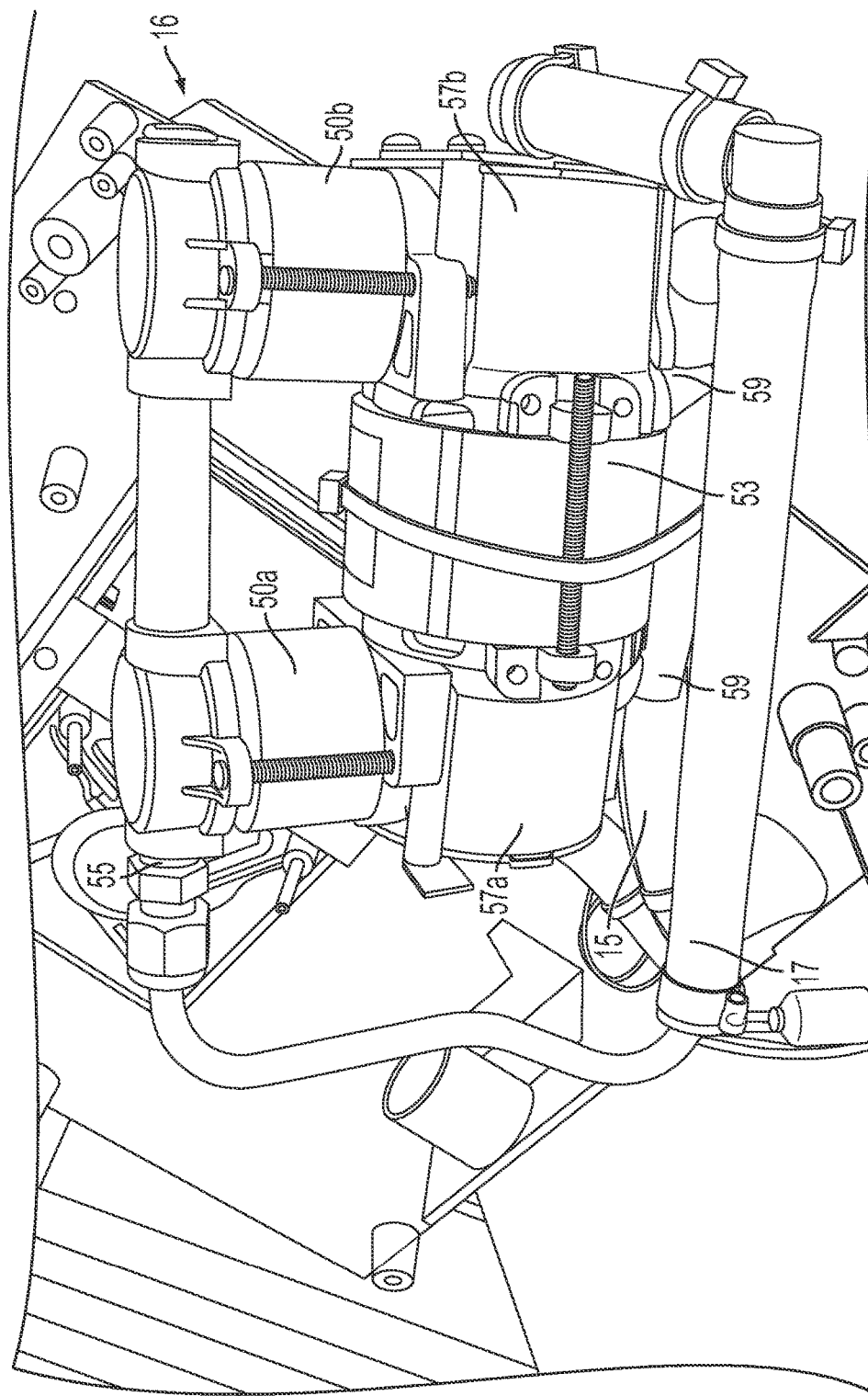
FIG. 3a is a detailed view of a compressor of the portable oxygen concentrator.
Figure 3B:
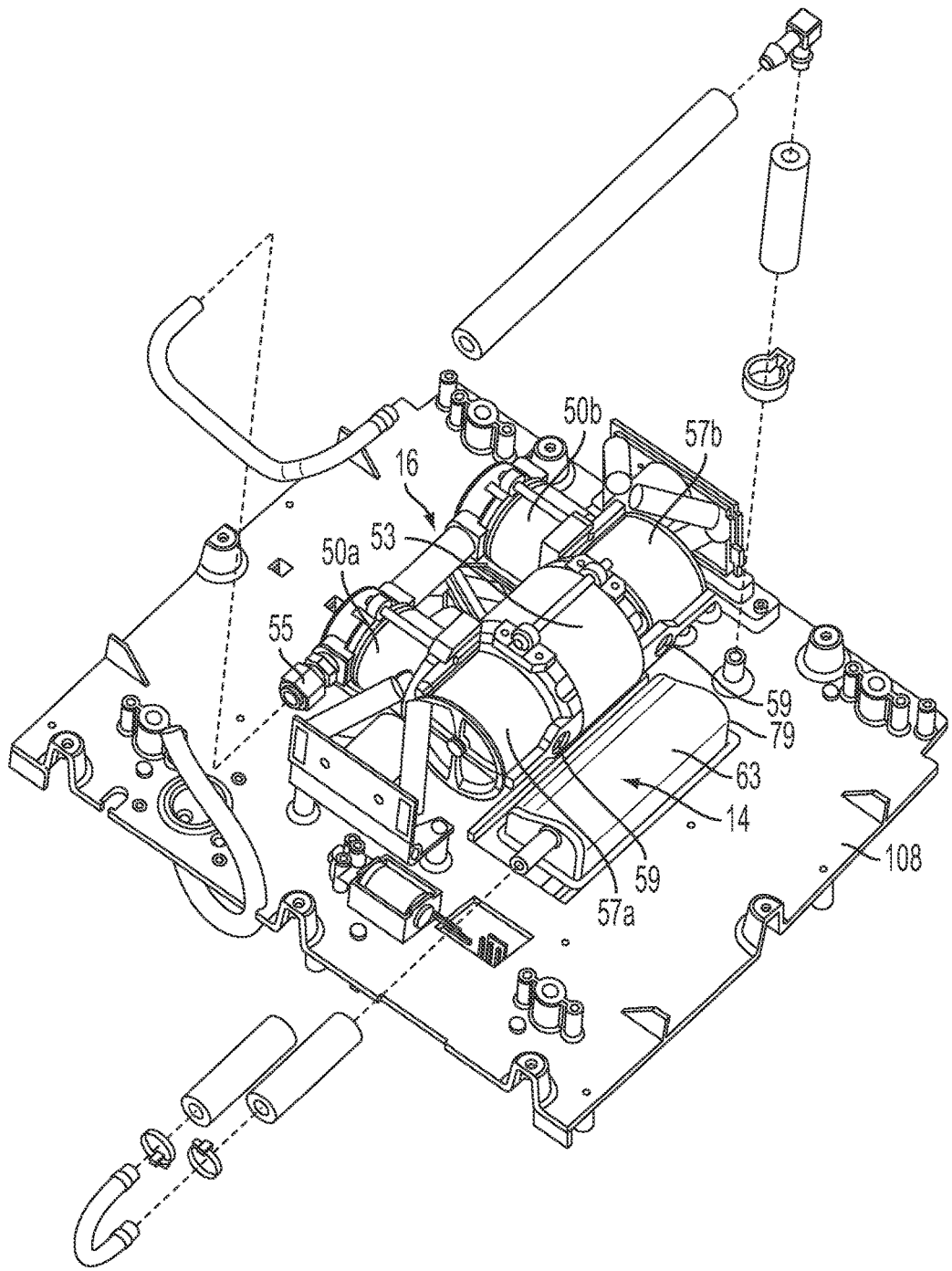
FIG. 3b is a detailed view of the compressor and an air filter supported on the support member of the portable oxygen concentrator.

FIGS. 3a and 3b shows an embodiment of compressor 16 of concentrator 10. Compressor 16 has two cylinders 50a, 50b (two are shown in this embodiment) for compressing the air received from the air supply. A compressor intake or inlet port 59 (two are shown in this embodiment) in the compressor 16 is configured to receive filtered air from the compressor passage 15. Pistons (not shown) are configured to reciprocate in cylinders 50a, 50b, respectively, so as to compress the fluid. Crank shafts (not shown) are housed within crank shaft housings 57a 57b and are configured to drive the pistons within the cylinders 50a, 50b. The pistons may be wobble (or WOB-L) pistons or other types of pistons. A motor 53 is operatively connected to the crank shafts and is configured to drive the crank shafts.

In one embodiment, the compressor assembly 16 has a tandem arrangement with two cylinders 50a 50b, each having a piston received therein. A motor shaft (not shown) may connect the motor 53 to the crankshafts, which are each connected to one of the two pistons, so that the movement of the pistons oppose each other. After the compressor 16 has compressed the air, the compressed air is communicated to the compressor outlet passage 17 (shown in FIG. 3a) through an outlet port 55 of the compressor 16. However, this embodiment is not intended to be limiting, and it is contemplated that compressor assembly 10 may have other arrangements and numbers of cylinders 50a, 50b. For example, compressor assembly 10 may be of single or dual acting designs. Compressor assembly 10 may also include more than two cylinders. It should be appreciated that the compressor 16 is not limited to this configuration and may be any type of compressor that compresses air.

Referring back to FIG. 2, the oxygen generating system 11 includes diaphragm valves 20. Although four diaphragm valves (20A, 20B, 20C, and 20D) are shown in this embodiment, it should be appreciated that the number of diaphragm valves may vary in other embodiments. A controller 21 is coupled to the air control valves 20 for selectively opening and closing the air control valves 20 to control airflow therethrough, and consequently, through sieve bed passages 19A, 19B to the sieve beds 18A, 18B. Sieve bed passages 19A, 19B are at least partially defined by pathways in air manifold 110. The air control valves 20 may be selectively opened and closed to provide flow paths, e.g., from compressor 16 to the sieve bed 18A, 18B through a compressor outlet passage 17 and/or from the sieve bed 18A, 18B through exhaust passages 23A, 23B to exhaust ports 22A, 22B. Accordingly, when supply air control valve 20B is open, a flow path may be defined from the compressor 16, through compressor passage 17, through air control valve 20B, through sieve bed passage 19A, and into the sieve bed 18A. When exhaust air control valve 20D is open, a flow path may be defined from the sieve bed 18B, through the sieve bed passage 19B, through the air control valve 20D, through an exhaust passage 23B, and out exhaust opening(s) 22A, 22B.

An exemplary two-way valve that may be used for each of valves 20 is the SMC DXT valve, available from SMC Corporation of America, of Indianapolis, Ind. The valve may be provided as "normally open." When pressure is applied to the top side of the diaphragm through the pilot valve, the diaphragm may be forced down onto a seat, shutting off the flow. Either a normally open or normally closed pilot solenoid valve may be used. Because the diaphragm valve itself is normally open, using a normally open solenoid valve may create normally closed overall operation, requiring application of electrical energy to open the valve.

In the embodiment shown in FIG. 2, oxygen generating system 11 includes at least one sieve bed 18A, 18B (two are shown in this embodiment) containing molecular sieve material configured to separate the pressurized air into a concentrated gas component for delivery to a subject. Sieve beds 18A, 18B include a first port 39A, 39B, respectively, configured to receive air and transfer nitrogen and a second port 43A, 43B, respectively, configured to transfer oxygen out of the sieve beds 18A, 18B. The sieve material may include one or more known materials capable of adsorbing nitrogen from pressurized ambient air, thereby allowing oxygen to be bled off or otherwise evacuated from the sieve beds 18A, 18b. Exemplary sieve materials that may be used include synthetic zeolite, LiX, and the like, such as UOP Oxysiv 5, 5A, Oxysiv MDX, or Zeochem Z10-06. Although two sieve beds 18A, 18B are shown in FIG. 2, it will be appreciated that one or more sieve beds may be provided, e.g., depending upon the desired weight, performance efficiency, and the like.

Sieve bed 18A, 18B may be purged or exhausted, i.e., first end 39A, 39B may be exposed to ambient pressure, once the pressure within the sieve bed 18A, 18B reaches a predetermined limit (or after a predetermined time). This causes the compressed nitrogen within sieve bed 18A, 18B to escape through first end 39A, 39B and to exit the exhaust ports 22A, 22B. Optionally, as sieve bed 18A, 18B is being purged, oxygen escaping from the other sieve bed 18A, 18B (which may be being charged simultaneously) may pass through a purge orifice 30 into second port 43A, 43B of purging sieve bed 18A, 18B, e.g., if the pressure within the charging sieve bed is greater than within the purging sieve bed, which may occur towards the end of purging. In addition or alternatively, oxygen may pass through check valves 28A, 28B located between the sieve beds 18A, 18B, e.g., when the relative pressures of the sieve beds 18A, 18B and reservoir 26 causes the check valves 28A, 28B to open, in addition to or instead of through the purge orifice 30.

Oxygen generating system 11 is configured operate the sieve beds 18A, 18B such that they are alternatively "charged" and "purged" to generate concentrated oxygen. When a sieve bed 18A or 18B is being charged or pressurized, compressed ambient air is delivered from the compressor 16 into first end 39A, 39B of sieve bed 18A, or 18B, causing the sieve material to adsorb more nitrogen than oxygen as sieve bed 18A or 18B is pressurized. While the nitrogen is substantially adsorbed by the sieve material, oxygen escapes through second ends 43A, 43B of sieve bed 18A or 18B, where it may be stored in the reservoir 26 and/or be delivered to the subject.

Exhaust ports 22A, 22B may be configured to expel exhaust air (generally concentrated nitrogen) from the sieve beds 18A, 18B. In one embodiment, the exhaust air may be directed towards controller 21 or other electronics within the concentrator 10, e.g., for cooling the electronics.

As further shown in FIG. 2, a purge orifice 30 may be provided between the sieve beds 18A, 18B. Purge orifice 30 may remain continuously open, thereby providing a passage for oxygen to pass from one sieve bed 18A, 18B to the other, e.g., while the one sieve bed 18A, 18B is charging and the other is purging. Purge orifice 30 may have a precisely determined cross-sectional size, which may be based upon one or more flow or other performance criteria of the sieve beds 18A, 18B. For example, the size of the purge orifice 30 may be selected to allow a predetermined oxygen flow rate between the charging and purging sieve beds 18A, 18B. It is generally desirable that the flow through the purge orifice 30 is equal in both directions, such that both sieve beds 18A, 18B may be equally purged, e.g., by providing a purge orifice 30 having a geometry that is substantially symmetrical.

Oxygen generating system 11 may also include an oxygen side balance valve 32 between sieve beds 18A, 18B configured to balance bed pressures in sieve bed 18A and sieve bed 18B so as to maximize efficiency (e.g., to reduce power consumption). During the pressure cycling of sieve beds 18A, 18B, the pressure in sieve bed 18A may be higher than the pressure in sieve bed 18B indicating that the beds are not balanced. In such an instance, balance valve 32 is operated (opened) to relieve some pressure from sieve bed 18A and provide the pressure to sieve bed 18B, for example, before compressor 16 switches from sieve bed 18A to sieve bed 18B to supply compressed air to sieve bed 18B. Transferring some pressure from sieve bed 18A to sieve bed 18B allows sieve bed 18B be at some intermediate pressure (rather than be at a zero pressure), when compressor starts supplying compressed air to sieve bed 18B.

As mentioned above, check valves 28A, 28B may open to enable oxygen to pass therethrough. Check valves 28A, 28B may simply be pressure-activated valves that provide one-way flow paths from the sieve beds 18A, 18B of the oxygen generating system 11 into reservoir 26 of the oxygen delivery system 13 through oxygen delivery passages 27A, 27B. Oxygen delivery passage 27A, 27B may be at least partially defined by pathways in oxygen manifold 112. Because the check valves 28A, 28B allow one-way flow of oxygen from the sieve beds 18A, 18B into the reservoir 26 and oxygen delivery passages 27A, 27B, whenever the pressure in either sieve bed 18A, 18B exceeds the pressure in the reservoir 26, the respective check valve 27A, 27B may open. Once the pressure within either sieve bed 18A, 18B becomes equal to or less than the pressure in reservoir 26, respective check valve 28A, 28B may close.

Oxygen delivery system 13 includes reservoir 26 that stores oxygen enriched gas and a connection portion 34 (e.g., a cannula barb) that connects to a subject interface (e.g., a cannula) for delivery of the oxygen to the subject. In an alternative embodiment, concentrator 10 may include multiple reservoirs (not shown) that may be provided at one or more locations within the concentrator. Concentrator 10 may also include one or more flexible reservoirs, e.g., bags or other containers that may expand or contract as oxygen is delivered into or out of them. The reservoirs may have predetermined shapes as they expand or more expand elastically to fill available space within the concentrator. Optionally, one or more rigid reservoirs may be provided that communicate with one or more flexible reservoirs (not shown), e.g., to conserve space within the concentrator.

In one embodiment, oxygen delivery system 13 includes a delivery passage or line 41 with a proportional oxygen delivery valve 36, a flow sensor 38, a pressure sensor 40, an oxygen sensor 42, a filter 44, a relief valve 46, and a pressure sensor 48 associated therewith. These components may be of the same type as described in U.S. provisional patent application No. 61/533,871, filed Sep. 13, 2011, the entire contents of which are incorporated herein in its entirety.

Oxygen delivery valve 36 may be configured to control the flow of oxygen through an oxygen delivery passage or line 41 from the reservoir 26 out of the concentrator 10 to a subject. The oxygen delivery valve may be a solenoid valve coupled to controller 21 that may be selectively opened and closed. An exemplary valve that may be used for the oxygen delivery valve 36 is the Hargraves Technology Model 45M, which may have a relatively large orifice size, thereby maximizing the possible flow through the oxygen delivery valve 36. Alternatively, it may also be possible to use a Parker Pneutronics V Squared or Series 11 valve.

Controller 21 may be configured to control when proportional oxygen delivery valve 36 is fully open, fully closed, or partially open as well as the degree to which valve is open based on the received inputs from the sensors. When oxygen delivery valve 36 is open, oxygen may flow through the oxygen delivery passage 41 and through the oxygen delivery valve 36 to the subject. Oxygen delivery valve 36 may be opened for desired durations at desired frequencies, which may be varied by the controller 21, thereby providing pulse delivery. Alternatively, controller 21 may maintain oxygen delivery valve 36 open to provide continuous delivery, rather than pulsed delivery. In this alternative, the controller may throttle oxygen delivery valve 36 to adjust the volumetric flow rate to the subject.

Pressure sensor 40 may be coupled to processor 23, e.g., to provide signals that may be processed by processor 23 to determine the pressure differential across oxygen delivery valve 36. Controller 21 may use this pressure differential to determine a flow rate of the oxygen being delivered from portable oxygen concentrator 10 or other parameters of oxygen being delivered. Controller 21 may change the frequency and/or duration that oxygen delivery valve 36 is open based upon the resulting flow rates, e.g., based upon one or more feedback parameters.

Flow sensor 38 may also be coupled to the processor 23 and configured to measure the instantaneous mass flow of the oxygen passing through delivery line 41 and to provide feed-back to proportional oxygen delivery valve 36. In one embodiment, flow sensor 38 is a mass flow sensor.

Oxygen sensor 42 may be coupled to the processor 23 and may generate electrical signals proportional to the purity that may be processed by the controller 21 and used to change operation of the concentrator 10. Because the accuracy of the oxygen sensor 42 may be affected by airflow therethrough, it may be desirable to sample the purity signals during no flow conditions, e.g., when proportional oxygen delivery valve 36 is closed.

Processor 23 of portable oxygen concentrator 10 may be configured to receive the signals from one or more sensing components of portable oxygen concentrator 10, e.g., flow sensor 38, pressure sensor 40, oxygen sensor 42 and/or pressure sensor 48.

Air filter 44 may include any conventional filter media for removing undesired particles from oxygen being delivered to the subject. The air filter may be provided either downstream or upstream of relief valve 46 and pressure sensor 48.

Relief valve 46 is configured to relieve pressure (open) responsive to the pressure within the supply line exceeding a predetermined threshold so as to decrease pressure within the supply line when oxygen is continuously supplied to the subject. Relief valve 46 may be similar to the relief valve described in U.S. provisional patent application No. 61/533, 912, filed Sep. 13, 2011, which is incorporated herein in its entirety.

Pressure sensor 48 may be configured to sense the pressure within the delivery line 41 so that inhalation of the subject may be detected. For example, the subject breathing rate may be determined by the controller 21, e.g., based upon pressure readings from the pressure sensor 48. Pressure sensor 48 may detect a reduction in pressure as the subject inhales. Controller 21 may monitor the frequency at which the pressure sensor 48 detects the reduction in pressure to determine the breathing rate. In addition, the controller 21 may also use the pressure differential detected by the pressure sensor. Pressure sensor 48 may be a piezo resistive pressure sensor capable of measuring absolute pressure. Exemplary transducers that may be used include the Honeywell Microswitch 24PC01SMT Transducer, the Sensym SX01, Motorola MOX, or others made by All Sensors. Because the pressure sensor 48 may be exposed to the full system pressure of the concentrator 10, it may be desirable for the over-pressure rating of pressure sensor 48 to exceed the full system pressure.

As mentioned above, concentrator 10 may emit a high level of noise, especially if oxygen demand for delivery to the subject is increased. The demand for oxygen may be associated with or based on a dose setting of the oxygen concentrator. The dose setting may be subject selected or predetermined. In one embodiment, the dose setting may include a quantitative and/or qualitative setting. Controller 22 may relate the subject-selected qualitative setting with a desired flow rate or bolus size, e.g., relating to the maximum flow capacity of apparatus 10. The settings may correspond to points within the range at which the apparatus 10 may supply concentrated oxygen. For example, a maximum flow rate (or equivalent flow rate of pure oxygen) for the apparatus 10 may be used. Alternatively, a maximum bolus volume may be used. A quantitative setting may allow a subject to select a desired flow rate, which may be an actual concentrated oxygen flow rate or an equivalent pure oxygen flow rate, or a desired bolus volume. The flow rates or volumes available for selection may also be limited by the capacity of apparatus 10, similar to the qualitative settings. As the dose setting is increased, the pulse duration may be increased to deliver a predetermined bolus during each pulse. If the subject's breathing rate remains substantially constant, the pulse frequency may also remain substantially constant, thereby increasing the overall flow rate being delivered to the subject. The flow rate may also be based upon the setting selected by the subject during continuous delivery.

Because of the various settings available, in one embodiment, oxygen concentrator 10 should be able to receive the required amount of air from the air supply when the concentrator 10 is at its highest setting. Accordingly, an air inlet opening 70 (see for example FIG. 4), which may be any inlet or opening that receives air from an air supply, such as ambient air, for pressurization by compressor 16, should be sized to accommodate the amount of air that passes therethrough when the concentrator 10 is at its highest settings. However, the sound in the oxygen concentrator 10 may primarily originate from inlet opening 70. The air inlet does not necessarily need to be compressor intake port 59 formed directly on compressor 16 (although it may be), but instead may be an opening to a part of a tube or passage or other component that is connected to and in communication with the compressor intake port 59. In some embodiments, the inlet opening may be the openings 12 of concentrator 10. In some embodiments, the inlet opening may also be an opening or inlet in a housing 63 (see FIG. 3b) of air filter 14 that is connected to and in communication with the compressor 16.

Figure 4:
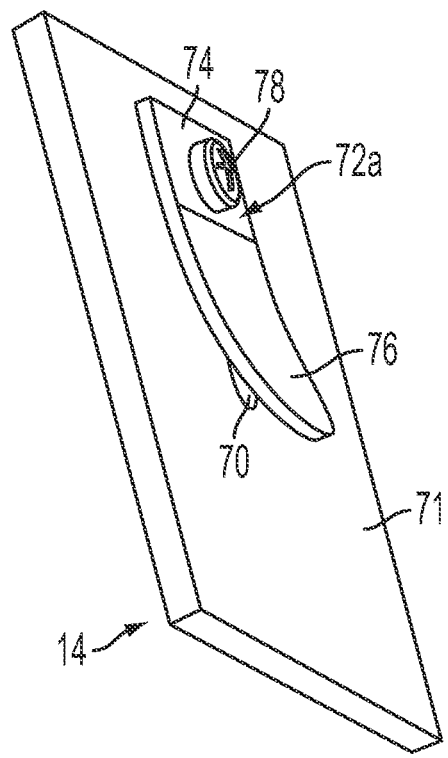
FIG. 4 is a detailed view of an embodiment of an inlet opening and inlet opening restrictor of the portable oxygen concentrator.

FIG. 4 shows a detailed perspective view of inlet opening 70 configured to receive air to be compressed by compressor 16. In this embodiment, inlet opening 70 takes the form of an opening formed in a wall 71 (see also FIG. 3b) of housing 63 of air filter 14. Referring back to FIG. 4, air filter 14 is connected to and in communication with the compressor inlet port of compressor 16 such that air received through inlet opening 70 is communicated to compressor 16 for pressurization by the compressor. As mentioned above, in other embodiments, inlet opening 70 may be provided elsewhere and/or on other components that is in communication with the compressor 16 such that air received by inlet 70 can be communicated to compressor 16. An inlet opening restrictor 72a is connected to air filter 14 and configured to dynamically change a characteristic of inlet opening 70 responsive to increased or decreased demand for the pressurized air. The characteristic may include one or more of size, shape, resistance, and/or other characteristics. For example, the restrictor 72a may be configured to dynamically change the size, shape, and/or resistance of the inlet opening 70 proportionately for some or all input/output settings.

In one embodiment, restrictor 72a includes a connection portion 74 and a restriction portion 76. A connection member 78, such as a screw, pin, or other connection members known in the art, may be used to connect restrictor 72a to the air filter 14. In the embodiment shown in FIG. 4, connection member 76 takes the form of a threaded screw. Restrictor 72a may be resilient so as to enable the restrictor to bend or flex in response to air flow, which will be described in more detail later. The restrictor may be made of plastic, silicone, rubber materials, or any other materials having resilient characteristics.

Restrictor 72a is configured to substantially block or close inlet opening 70 (see FIG. 5a) when there is no or low air flow through the inlet opening or in other words, when substantially no air is being received by inlet opening 70. In one embodiment, when substantially no air is received by inlet opening 70 (for example, when the concentrator 10 is off or not in use), restrictor 72a may completely block or close the inlet opening. Accordingly, the size of opening 70 is restricted and substantially no sound is emitted from the inlet opening.

Decreasing or restricting the size of the opening 70 may reduce the sound level output of the concentrator 10. Thus, when demand for oxygen is low (e.g., when the concentrator 10 is on a low setting), the size of the inlet opening 70 may be effectively decreased using the restrictor 72a to reduce the level of the sound output. However, as demand for oxygen increases (e.g., the concentrator 10 is set to a higher setting), the air flow through the inlet opening 70 may also increase, and the restrictor 72a may be configured to effectively increase the size of the inlet opening 70 accordingly, which will be described later. Other enhancements may be provided by restrictor 72a.

Figure 5A:
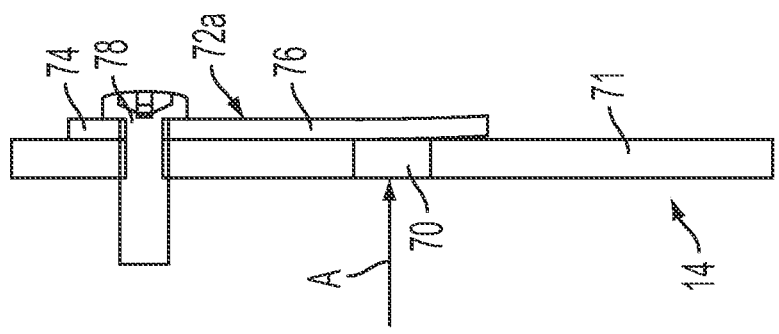
FIGS. 5a-5c are cross sectional side views of the inlet opening and inlet opening restrictor of the portable oxygen concentrator in accordance with the embodiment of FIG. 4.
Figure 5B:
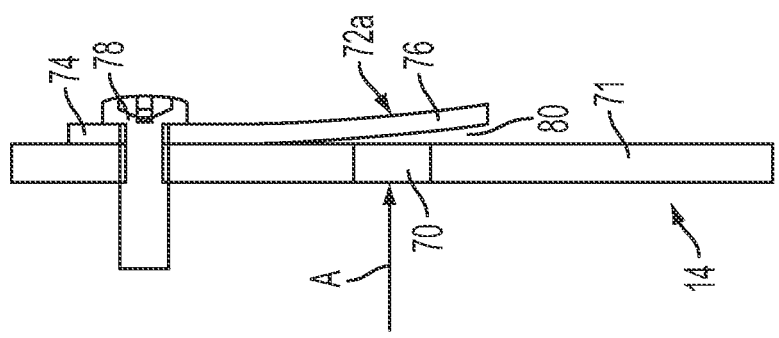

FIG. 5a shows an embodiment of restrictor 72a in a default, relaxed position wherein restrictor 72a contacts wall 71 of the air filter 14 such that the restrictor substantially closes or blocks inlet opening 70. Thus, the size of the opening is minimized to reduce the level of noise output. As air flows through inlet opening 70 in the direction of A and the rate and/or amount of air flow is increased, restrictor 72a is configured to flex or move further away from wall 71 by the force of the air flow such that a space 80 is defined between wall 71 and restrictor 72a, as shown in FIG. 5b. The air may flow into air filter 14 via opening 70 and through space 80. In effect, the size of the opening is increased from that of FIG. 5a to enable the increased air flow to pass therethrough. Accordingly, the size of space 80 may increase or decrease, and in effect, the size of the opening 70 may increase or decrease, depending on the air flow.

As the oxygen demand for delivery to the subject is increased (e.g., concentrator 10 is set to a higher setting), the air flow through opening 70 in the direction of A is increased. As a result, restrictor 72a may flex or bend further away from wall 71 of air filter 14, and thus increase the size of space 80, and in effect, increase the size of inlet opening 70, as shown in FIG. 5c.

Figure 5C:
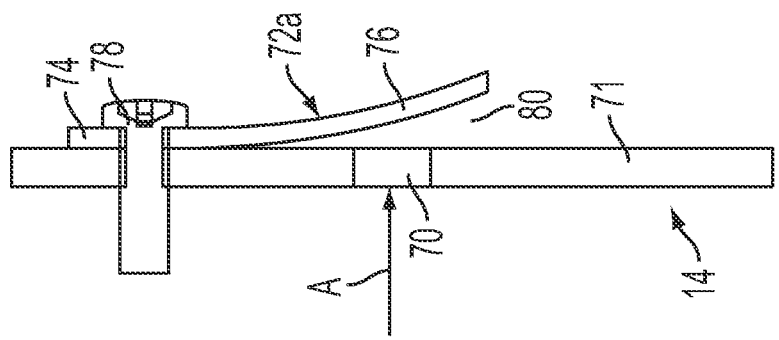

Accordingly, in the embodiment shown in FIGS. 5a-5c, the restrictor 72a is configured to bend or flex further away from the wall 71 when the air flow through the opening 70 is increased so as to effectively increase the size of the opening 70 and move towards the wall 71 (e.g., due to the resiliency of the restrictor 72a) when the air flow through the opening 70 is decreased so as to effectively decrease the size of the opening 70. In some embodiments, the amount of movement of the restrictor 72 relative to the wall 71 may be proportional to the amount of oxygen desired and the amount of air flow passing through the inlet opening 70. Restrictor 72a may dynamically change the characteristics, such as size or shape, of the inlet opening 70 in accordance with the amount of air flow through the inlet opening 70.

By effectively reducing the size and/or shape of inlet opening 70 when less air moves through the opening, restrictor 72a may set the inlet opening to its smallest optimal size, thus reducing sound level output. In other words, the size of inlet opening 70 is minimized and sized optimally for the sound level output and for the amount of air flow that passes therethrough. This enables the inlet opening to be reduced in size and the sound output to be minimized when concentrator 10 is at its lowest setting, and inlet opening 70 to be increased in size when the concentrator is at its higher settings.

Figure 6:
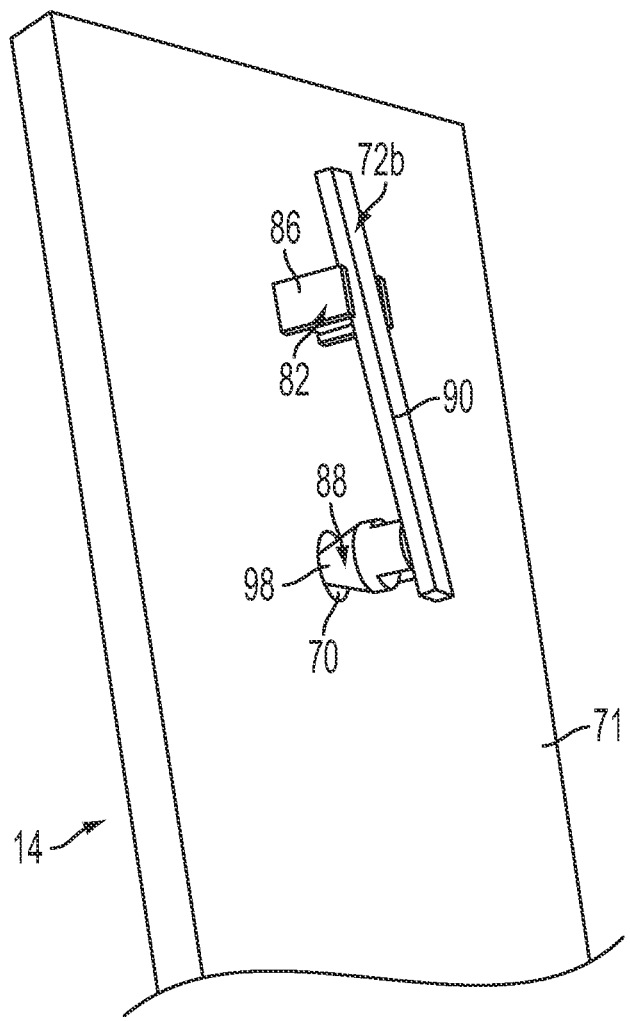
FIG. 6 is a detailed view of another embodiment of the inlet opening and inlet opening restrictor of the portable oxygen concentrator.
Figure 7C:
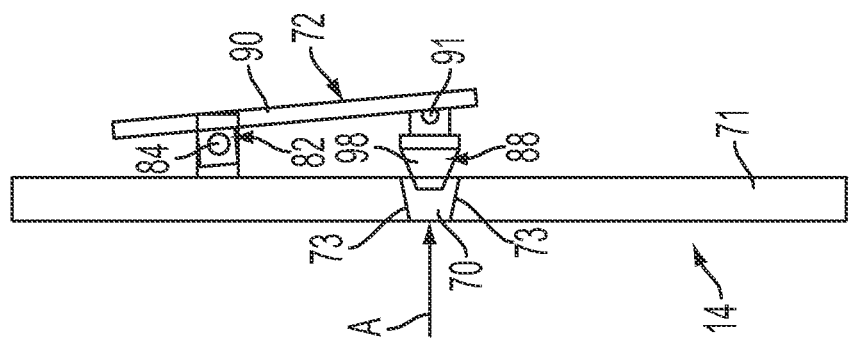
FIGS. 7a-7c are cross sectional side views of the inlet opening and inlet opening restrictor of the portable oxygen concentrator in accordance with the embodiment of FIG. 6.

FIG. 6 shows another embodiment of a restrictor 72b. In this embodiment, the restrictor 72b is pivotally connected to the wall 71 of the air filter 14 via a pivot or hinge structure 82. A biasing element (not shown), such as a spring, may bias the restrictor 72b in a default position as shown in FIG. 7a. A pivot pin 84 (see FIG. 7a) may be used to pivotally connect the restrictor 72b to an extending portion 86 (see FIG. 6) of the air filter 14. However, it should be appreciated this is not intended to be limiting and that any connection structure known in the art to pivotally connect the restrictor 72b may be used. In this embodiment, restrictor 72b includes a contact portion 88, which takes the form of a plunger in this embodiment, configured to be inserted or removed from the inlet opening 70 so as to dynamically change a characteristic (e.g., size and/or shape) of the inlet opening 70. Contact portion 88 may be connected to a main body portion 90 of restrictor 72b via a pivot pin 91 (see FIG. 7a). Contact portion 88 may be made of rubber, silicone, plastic, other materials, or any combination thereof.

As shown in FIG. 7a, plunger 88 may have a first end 94 located closer to main body 90 of restrictor 72b and a second end 96 opposite first end 94. A sloped or beveled surface 98 may be defined between the first and second ends 94, 96 such that a cross sectional area of the first end 94 is larger than a cross sectional area of the second end 96. Wall 71 may also have a beveled surface 73 defining the inlet opening 70.

Restrictor 72b is configured to change a characteristic, such as size and/or shape, of the inlet opening 70 responsive to increased or decreased oxygen demand, which will be described in more detail below. Restrictor 72b may be used to optimize the size and/or shape of inlet opening 70 according to the demand for the oxygen to minimize the sound level output. That is, restrictor 72b may be used to minimize the size and/or shape of inlet opening 70. When more oxygen is desired and the air flow is increased, the force of the air flow may be stronger than the biasing force of the biasing element, thus moving restrictor 72b away from wall 71 so as increase the size or change the shape of inlet opening 70 in order to enable more air to flow therethrough. When less oxygen is desired and the air flow is decreased, restrictor 72b may be biased closer towards wall 71 by the biasing element so as to decrease the size or change the shape of inlet opening 70 in order to decrease the sound level output.

As shown in FIG. 7a, when substantially little or no air flow is passing through inlet opening 70c, restrictor 72b is in the default position wherein the contact portion 88 of restrictor 72b is received in inlet opening 70 such that inlet opening 70 is substantially closed or blocked. In one embodiment, when restrictor 72b substantially closes the inlet opening 70, at least a portion of the beveled surface 98 of the contact portion 88 is in contact with at least a portion of the beveled surface 73 of the air filter 14 that defines the inlet opening 70. Thus, the sound level output of the concentrator 10 is minimized.

Figure 7B:
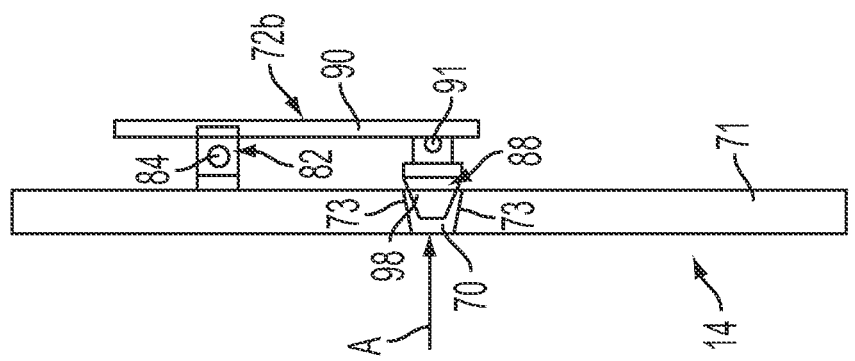
Figure 7A:
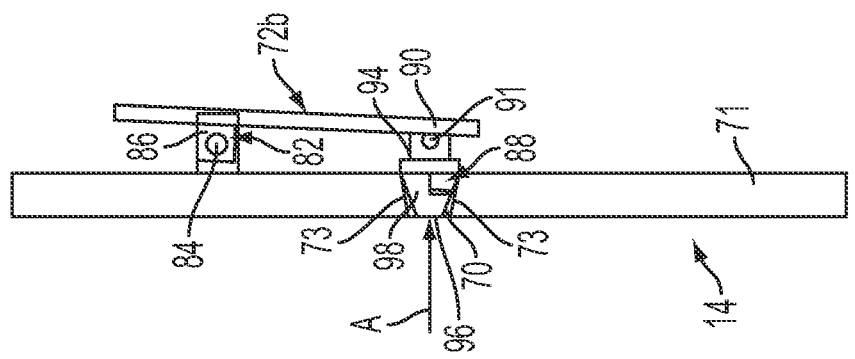

When more oxygen is desired and the air flow through inlet opening 70 is increased as a result, the air flow may push restrictor 72b away from wall 71 of air filter 14, as shown in FIG. 7b. Restrictor 72b may pivot along pivot structure 84 and contact portion 88 may pivot along pivot pin 91 during this movement. As contact portion 88 moves away from inlet opening 70, the shape and/or size of inlet opening 70 is increased to enable the increased air flow to pass therethrough. However, inlet opening 70 may still be restricted at least partially by contact portion 88, which is still partially received within inlet opening 70, as shown in FIG. 7b. Thus, the size of the inlet opening is sized optimally for air flow and for the sound output level.

As oxygen demand is further increased and the air flow is increased as a result, the increased air flow may push the restrictor 72b further away from the wall 71, as shown in FIG. 7c. As a result, the contact portion 88 may be pushed further away from the wall 71 than in FIG. 7b and the size/shape of the inlet opening 70 may be effectively increased due to the further removal of the contact portion 88 from the inlet opening 70. In some embodiments, the contact portion 88 may be completely removed from the inlet opening 70. When the air flow decreases (e.g., the concentrator 10 is set to a lower setting), the biasing element may move the restrictor 72b towards the wall 71 such that the contact portion 88 of the restrictor 72b is further received in the inlet opening 70. Thus, the relative position of the contact portion 88 of the restrictor 72 and the inlet opening 70 enables the inlet opening 70 to dynamically change in shape and/or size according to changing oxygen demand and changing air flow.

It should be appreciated that the above described embodiments of restrictor 72a, 72b are not intended to be limiting. The restrictor may take any other forms or configurations that enables a characteristic of the inlet opening 70 to be dynamically changed. For example, while restrictor 72a and/or 72b have been described as passive elements that dynamically adapt to airflow based on material and/or structural properties of the restrictor, this is not intended to be limiting. In some implementations, the restrictor may be an active element that is controlled by a controller 21 based on a measured airflow and/or an intended airflow through inlet opening 70.

It should be appreciated that any of the passages described herein may be any type and combination of conduits, tubes, or other structures that enable air or other fluids to pass therethrough. In some embodiments, the passages may be built into the support member 108, air manifold 110, or delivery manifold 112 described in U.S. provisional patent application No. 61/533,962, filed Sep. 13, 2011.

Concentrator 10 may be operated and controlled by a controller 21 that includes one or more hardware components and/or software modules that control one or more aspects of the operation of portable oxygen concentrator 10. Controller 21 may be coupled to one or more components of portable oxygen concentrator 10, e.g., compressor 16, air control valves 20, and/or oxygen delivery valve 36. Controller 21 may also be coupled to one or more components of oxygen concentrator 10, such as the sensors, valves, or other components. The components may be coupled by one or more wires or other electrical leads capable of receiving and/or transmitting signals between controller 21 and the components.

Controller 21 may also be coupled to a subject interface (not shown), which may include one or more displays and/or input devices. The subject interface may be a touch-screen display that may be mounted to portable oxygen concentrator 10. The subject interface may display information regarding parameters related to the operation of portable oxygen concentrator 10 and/or allow the subject to change the parameters, e.g., turn portable oxygen concentrator 10 on and off, change dose setting or desired flow rate, etc. Portable oxygen concentrator 10 may include multiple displays and/or input devices, e.g., on/off switches, dials, buttons, and the like (not shown). The subject interface may be coupled to controller 21 by one or more wires and/or other electrical leads (not shown for simplicity), similar to the other components.

Controller 21 may include a single electrical circuit board that includes a plurality of electrical components thereon. These components may include one or more processors 23, memory, switches, fans, battery chargers, and the like (not shown) mounted to the circuit board. It will be appreciated that controller 21 may be provided as multiple subcontrollers that control different aspects of the operation of portable oxygen concentrator 10. For example, a first subcontroller may control operation of compressor 16 and the sequence of opening and closing of air control valves 20, e.g., to charge and purge sieve beds 12 in a desired manner. Additional information on an exemplary first subcontroller that may be included in portable oxygen concentrator 10 may be found in U.S. Pat. No. 7,794,522, the entire disclosure of which is expressly incorporated by reference herein.

Portable oxygen concentrator 10 may include one or more power sources, coupled to the controller 21, processor 23, compressor 16, air control valves 20, and/or oxygen delivery valve 36. For example, a pair of batteries (not shown) may be provided that may be mounted or otherwise secured to portable oxygen concentrator 10. Mounts, straps or supports (not shown) may be used to secure the batteries to portable oxygen concentrator 10. Additional information on exemplary batteries that may be included in portable oxygen concentrator 10 may be found in U.S. Pat. No. 7,794,522, the entire disclosure of which is expressly incorporated by reference herein. The controller 21 may control distribution of power from batteries to other components within portable oxygen concentrator 10. For example, the controller 21 may draw power from one of the batteries until its power is reduced to a predetermined level, whereupon controller 21 may automatically switch to the other of the batteries.

Optionally, portable oxygen concentrator 10 may include an adapter such that an external power source, e.g., a conventional AC power source, such as a wall outlet, or a portable AC or DC power source, such as an automotive lighter outlet, a solar panel device, and the like (not shown). Any transformers or other components (also not shown) necessary to convert such external electrical energy such that it may be used by portable oxygen concentrator 10 may be provided within portable oxygen concentrator 10, in the cables connecting portable oxygen concentrator 10 to the external power source, or in the external device itself.

It should be appreciated that the embodiment of the portable oxygen concentrator 10 described is not intended to be limiting. The portable oxygen concentrator 10 may include one or more additional components, e.g., one or more check valves, filters, sensors, electrical power sources (not shown), and/or other components, at least some of which may be coupled to the controller 21 (and/or one or more additional controllers, also not shown), as described further below. It should be appreciated that the terms "airflow," "air," or "gas" are used generically herein, even though the particular fluid involved may be ambient air, pressurized nitrogen, concentrated oxygen, and the like.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An oxygen concentrator comprising:
    an inlet opening configured to receive air, the inlet opening formed in a wall of the oxygen concentrator;
    a compressor configured to pressurize the air received through the inlet opening;
    an inlet opening restrictor configured to dynamically change a characteristic of the inlet opening responsive to increased or decreased demand for the pressurized air by a subject, the inlet opening restrictor comprising a connection portion coupled with the wall and an opposing restriction portion that is free, the inlet opening restrictor permitting air to flow in a first direction, and preventing air to flow in a second direction that is opposite of the first direction, the restriction portion being configured to move between a relaxed position and an open position, the restriction portion configured to block airflow through the inlet opening responsive to being in the relaxed position and permit airflow through the inlet opening responsive to being in the open position, the restriction portion being held in the open position by the airflow through the inlet opening, and wherein the relaxed position is a default position of the restriction portion in the absence of airflow; and
    a sieve bed configured to separate the pressurized air into a concentrated gas component for delivery to the subject.

2. The oxygen concentrator of claim 1, wherein the inlet opening restrictor is configured to pivot relative to the inlet opening.

3. The oxygen concentrator of claim 2, wherein the inlet opening restrictor is pivoted at the connection portion.

4. The oxygen concentrator of claim 1, wherein the characteristic of the inlet opening comprises a size of the inlet opening.

5. The oxygen concentrator of claim 1, wherein the demand for pressurized air is associated with a dose setting of the oxygen concentrator.

6. The oxygen concentrator of claim 1, wherein the inlet opening restrictor comprises a contact portion configured to be inserted or removed from the inlet opening so as to dynamically change the characteristic of the inlet opening.

7. The oxygen concentrator of claim 1, wherein the inlet opening restrictor is configured to change a shape of the inlet opening in a dynamic fashion.

8. The oxygen concentrator of claim 1, wherein the first direction corresponds to air flowing from ambient atmosphere into the oxygen concentrator.

9. A method of reducing a noise level in an oxygen concentrator, the method comprising:
    receiving air at an inlet opening in a wall of an oxygen concentrator;
    pressurizing the air using a compressor;
    changing a characteristic of the inlet opening responsive to increased or decreased demand for the pressurized air by a subject, the characteristic being changed by an inlet opening restrictor, the inlet opening restrictor comprising a connection portion coupled with the wall and an opposing restriction portion that is free, the inlet opening restrictor permitting air to flow in a first direction, and preventing air to flow in a second direction that is opposite of the first direction, the restriction portion being configured to move between a relaxed position and an open position, the restriction portion configured to block airflow through the inlet opening responsive to being in the relaxed position and permit airflow through the inlet opening responsive to being in the open position, the restriction portion being held in the open position by the airflow through the inlet opening, and wherein the relaxed position is a default position of the restriction portion in the absence of airflow; and
    separating the pressurized air into a concentrated gas component for delivery to the subject, the separation being provided by a sieve bed.

10. The method claim 9, wherein the inlet opening restrictor is configured to pivot relative to the inlet opening.

11. The method claim 9, wherein the characteristic of the inlet opening comprises a size of the inlet opening.

12. The method claim 9, wherein the demand for pressurized air is associated with a dose setting of the oxygen concentrator.

13. The method claim 9, wherein the inlet opening restrictor comprises a contact portion configured to be inserted or removed from the inlet opening so as to dynamically change the characteristic of the inlet opening.

14. A system configured to concentrate oxygen, the system comprising:
    means for receiving air in a wall of an oxygen concentrator;
    compressing means for pressurizing the air;
    means for changing a characteristic of the means for receiving responsive to increased or decreased demand for pressurized air by a subject, the means for changing comprising a connection portion coupled with the wall and an opposing restriction portion that is free, the means for changing the characteristic permitting air to flow in a first direction, and preventing air to flow in a second direction that is opposite of the first direction, the restriction portion being configured to move between a relaxed position and an open position, the restriction portion configured to block airflow through the means for receiving responsive to being in the relaxed position and permit airflow through the means for receiving responsive to being in the open position, the restriction portion being held in the open position by the airflow through the means for receiving, and wherein the relaxed position is a default position of the restriction portion in the absence of airflow; and means for separating the pressurized air into a concentrated gas component for delivery to the subject.

15. The system of claim 14, wherein the means for changing is configured to pivot relative to the means for receiving.

16. The system of claim 14, wherein the characteristic of the means for receiving comprises a size of the means for receiving.

17. The system of claim 14, wherein the demand for pressurized air is associated with a dose setting of the oxygen concentrator.

18. The system of claim 14, wherein the means for changing comprises a contact portion configured to be inserted or removed from the means for receiving so as to dynamically change the characteristic of the means for receiving.

* * * * *